US010610290B2

(12) United States Patent
Bjorn-Rasmussen et al.

(10) Patent No.: US 10,610,290 B2
(45) Date of Patent: Apr. 7, 2020

(54) SURGICAL INSTRUMENT

(71) Applicant: LINA MEDICAL INTERNATIONAL OPERATIONS AG, Root D4 (CH)

(72) Inventors: Peter Bjorn-Rasmussen, Glostrup (DK); Henrik Bisgaard Poulsen, Slangerup (DK)

(73) Assignee: LINA MEDICAL INTERNATIONAL OPERATIONS AG, Root D4 (CH)

( * ) Notice: Subject to any disclaimer, the term of this patent is extended or adjusted under 35 U.S.C. 154(b) by 112 days.

(21) Appl. No.: 15/536,618

(22) PCT Filed: Dec. 15, 2015

(86) PCT No.: PCT/EP2015/079854
§ 371 (c)(1),
(2) Date: Jun. 15, 2017

(87) PCT Pub. No.: WO2016/096894
PCT Pub. Date: Jun. 23, 2016

(65) Prior Publication Data
US 2017/0367753 A1    Dec. 28, 2017

(30) Foreign Application Priority Data

Dec. 16, 2014 (DK) .................................. 2014 70789

(51) Int. Cl.
*A61B 18/14* (2006.01)
*A61B 17/295* (2006.01)
(Continued)

(52) U.S. Cl.
CPC ........ *A61B 18/1445* (2013.01); *A61B 17/295* (2013.01); *A61B 18/1482* (2013.01);
(Continued)

(58) Field of Classification Search
CPC .............. A61B 18/1445; A61B 17/295; A61B 18/1482; A61B 2090/031;
(Continued)

(56) References Cited

U.S. PATENT DOCUMENTS

2003/0018331 A1* 1/2003 Dycus ................ A61B 18/1445
606/48
2006/0190035 A1* 8/2006 Hushka .............. A61B 17/2909
606/205
(Continued)

FOREIGN PATENT DOCUMENTS

| EP | 2 389 886 A1 | 11/2011 | |
|----|----|----|----|
| EP | 2389886 A1 * | 11/2011 | ......... A61B 18/1445 |
| EP | 2 606 845 A1 | 6/2013 | |
| EP | 2606845 A1 * | 6/2013 | ......... A61B 18/1206 |

(Continued)

Primary Examiner — Linda C Dvorak
Assistant Examiner — Christine A Dedoulis
(74) Attorney, Agent, or Firm — Muncy, Giessler, Olds & Lowe, PC

(57) ABSTRACT

A handheld electrosurgical instrument with jaws at a distal end of a shaft. For moving the jaws, the instrument includes a linkage structure with at least three pivots which are movable relative to the housing and with at least pivot which is fixed to the housing. By this arrangement, one of the movable pivots may move as a substitute for movement of the jaws, and the instrument may therefore always have the same limits for handle movement e.g. also if the jaws are prevented from moving. Additionally, a more uniform closure pressure may be ensured independently on the force applied to the handle.

21 Claims, 9 Drawing Sheets

(51) Int. Cl.
  *A61B 17/29* (2006.01)
  *A61B 18/00* (2006.01)
  *A61B 90/00* (2016.01)
  *A61B 17/00* (2006.01)

(52) U.S. Cl.
  CPC ............... *A61B 2017/00845* (2013.01); *A61B 2017/292* (2013.01); *A61B 2017/2919* (2013.01); *A61B 2018/0013* (2013.01); *A61B 2018/00577* (2013.01); *A61B 2018/00589* (2013.01); *A61B 2018/00595* (2013.01); *A61B 2018/00601* (2013.01); *A61B 2018/00916* (2013.01); *A61B 2018/1455* (2013.01); *A61B 2090/031* (2016.02); *A61B 2090/08021* (2016.02)

(58) Field of Classification Search
  CPC .. A61B 2017/00845; A61B 2017/2919; A61B 2017/292; A61B 2018/0013; A61B 2018/00577; A61B 2018/00589; A61B 2018/00595; A61B 2018/00601; A61B 2018/00916; A61B 2018/1455
  See application file for complete search history.

(56) References Cited

U.S. PATENT DOCUMENTS

| | | | | |
|---|---|---|---|---|
| 2007/0142833 | A1* | 6/2007 | Dycus | A61B 18/1445 606/51 |
| 2010/0030029 | A1* | 2/2010 | Markham | A61B 17/29 600/146 |
| 2010/0063527 | A1* | 3/2010 | Beaupre | A61B 17/320092 606/169 |
| 2010/0179545 | A1* | 7/2010 | Twomey | A61B 18/1445 606/51 |
| 2011/0082471 | A1* | 4/2011 | Holcomb | A61B 17/0401 606/139 |
| 2012/0172924 | A1* | 7/2012 | Allen, IV | A61B 17/29 606/205 |
| 2012/0316601 | A1* | 12/2012 | Twomey | A61B 18/1445 606/205 |
| 2013/0267951 | A1* | 10/2013 | Twomey | A61B 18/1445 606/46 |

FOREIGN PATENT DOCUMENTS

| | | | |
|---|---|---|---|
| WO | WO 97/05829 A1 | 2/1997 | |
| WO | WO-9705829 A1 * | 2/1997 | ......... A61B 18/1442 |

\* cited by examiner

SURGICAL INSTRUMENT

INTRODUCTION

The invention relates to a handheld surgical instrument for cutting, cauterizing, or coagulating tissue. Particularly, the invention relates to an instrument comprising:
- a housing forming a fixed grip;
- a handle movable relative to the fixed grip;
- a shaft extending in a longitudinal direction from a proximal end to a distal end, the proximal end being attached to the housing;
- a jaw assembly comprising first and second jaw members attached to the distal end of the shaft and being movable relative to each other between an open position where tissue can be received between the jaw members and a closed position where the tissue can be fixed between the jaw members, the jaw assembly further comprising a rod movably arranged in the shaft and configured for moving the jaws between the open and the closed positions; and a linkage structure for transferring force from the handle to the rod.

Known devices for laparoscopic or open electrosurgery sometimes include moveable jaws by which tissue can be immobilized. The jaws may have electrodes for electrosurgical coagulation of tissue and blood vessels. Additionally, the devices may include a knife which can be moved between the jaws for cutting the tissue after the coagulation.

Devices of this kind are sometimes referred to as electrosurgical forceps, advanced forceps, or monopolar or bipolar forceps.

The known devices typically include a handle which is movable to open and close the jaws. Mainly due to mechanical constraints, due to resistance against movement of the handle, and for other reasons, the jaws of the existing devices are not always moved very precisely and it can be difficult for the surgeon to determine when the tissue is compressed sufficiently between the jaws for the occlusion to begin. Moreover, the existing devices provide different compression pressure and they are not always capable of delivering a desired pressure, e.g. for occlusion of blood vessels.

SUMMARY

It is an object of embodiments of the invention to improve the ergonomic conditions for the user of electrosurgical forceps, to improve the ability to predict the compression pressure between the jaws, to allow faster operation of the jaws, to reduce the risk of malfunction and breakage, and to enable locking of the jaws in a closed position in a safe, reliable, and simple manner.

Accordingly, the invention, in a first aspect, provides an instrument of the kind mentioned in the introduction where the linkage structure comprises at least a first, a second, and a third floating pivots (12, 13, 17) each being movable relative to the housing, and at least one fixed pivot (15, 18) being attached to the housing;
where:
the first pivot is connected to the second pivot by a first element;
the first pivot is connected to one of the at least one fixed pivots by a second element;
the handle connects the second pivot and the third pivot; and
the third pivot is connected to a primary one of the at least one fixed pivots by an actuator element which is arranged to move the rod in the shaft upon rotation about the primary fixed pivot.

Due to the claimed linkage structure, movement of the handle towards the grip may either move the actuator element and thereby the jaws, or it may move the first pivot which is a floating pivot and thereby movable relative to the housing.

Due to the claimed linkage structure, the first pivot can therefore move as a substitute for movement of the rotatable actuator element. The device according to the invention may thereby facilitate, that the surgeon may experience a more uniform counter force against movement of the handle and he may experience fixed limits for movement of the handle relative to the grip even when the jaws are prevented from reaching the closed position, e.g. due to large tissue fragments between the jaws. This will generally be perceived as improved ergonomic conditions. If the jaws, for some reason, are prevented from moving further towards each other, the movement of the rotatable actuator element may stop while the first pivot moves as a substitute during continued movement of the handle relative to the fixed grip.

As a result thereof, the surgeon may continue moving the handle towards the grip without experiencing any unpleasant blocking of the handle, and it is possible always to ensure the same compression force between the jaws, and it is possible to prevent excessive force on the tissue. Additionally, breakage or damage of the mechanical structure of the device can be prevented by movement of the first pivot as a substitute for the movement of the jaws.

The pivots form joints between two elements of the instrument. Herein, a pivot is "a center point or axis of rotation of two elements relative to each other". The pivots may be defined by mechanical hinges with a hinge pin forming a well-defined axis of rotation and thereby a well-defined position of the pivot, or it may be defined by elastically deformable elements located between adjacent rigid elements—this kind of structure is sometimes referred to as a living hinge and creates a less well defined position of the pivot.

Herein, floating pivot means that the pivot can move relative to the housing. The fixed pivot, on the contrary, is not movable relative to the housing—i.e. the center point or axis of rotation remains in a fixed location relative to the housing and provides rotation of one element relative to another element about that fixed point or axis. The fixed pivot may e.g. be formed by a hinge having a hinge pin which is received in a fixed seat in the housing.

The elements should be capable of transferring a force, and they are therefore typically rigid elements. One element may be constituted by the housing, and another element may be constituted by the handle. At least one of the first, second, and third elements may be a rigid, elongated, bar or rod shaped element extending primarily in one direction.

The housing may e.g. form an outer shell which encapsulates at least a part of the linkage structure. The fixed grip may e.g. be a rear portion of the housing which could have a curved shape to match the palm of the user. The housing may e.g. comprise two shells which together encapsulate the linkage structure and which form the grip.

The handle is movable relative to the fixed grip and it is preferably shaped and positioned such that the fingers of one hand can catch the handle while the fixed grip leans against the palm of the same hand. The handle may not necessarily be attached directly to the housing but it may merely constitute, or be attached to the linkage structure in such a way that the handle thereby connects the second and third pivots. The handle may e.g. include a rigid element which extends between the second and third pivots.

The shaft may be removable to facilitate jaw replacement, or it may be non-removable from the housing. In fact, all elements, including the housing, the jaws, the shaft, and the handle may be un-separable and prepared for one-time usage, i.e. separation may require destruction.

The shaft may be rotatable relative to the housing about the longitudinal direction. In one embodiment, the shaft and housing are constituted by one and the same entity where the shaft is an elongated element of the entity and the housing forms a proximal body of the entity whereby the rod can be housed in the shaft and the linkage structure can be housed in the housing.

The jaw assembly comprises first and second jaw members, e.g. molded in a metal or plastic material and comprising electrodes for electrosurgical purpose. The jaws are attached to the distal end of the shaft. By means of a hinge, the jaws are movable relative to each other between an open position where tissue can be received between the jaw members and a closed position where the tissue can be fixed between the jaw members. Movement is effected by translational movement of the rod in the shaft.

Each jaw forms an electrode in electrical communication with, or electrically attachable to, a generator of an electrosurgical signal, e.g. an electric current signal, an electric voltage signal or a combination thereof, and the signal is a DC or AC signal such as an LF, an HF or an RF signal for instance a VHF, a UHF or a microwave signal, e.g. in the frequency range of 30 kHz-10 GHz.

The electrodes are primarily intended for coagulation, and a separate knife which is movable between the jaws may facilitate cutting of the coagulated tissue. The handle and/or the grip may include a switch for activating the electrical signal, and the instrument may further comprise a trigger for moving the separate knife back and forth in the space between the jaws.

In one embodiment, the electrodes may also be used for cutting the tissue, or a separate set of electrodes may be provided for cutting the tissue. For that purpose, the electrodes or the optional two sets of electrodes may receive at least two different signals, e.g. one for cutting and one for coagulation. For the purpose of switching between the at least two different signals, first and second electric powers may be obtained by means of a switch, e.g. incorporated in the handle or in the grip.

Although any suitable values of the electric power and any suitable signal frequency may be utilized for various purposes, in on embodiment of the invention, the first and/or second electric powers are delivered by a 40 watt 900 kHz generator.

The jaw assembly may further comprise a rod movably arranged in the shaft and configured for moving the jaws between the open and closed positions. The jaws may particularly be closed by movement of the rod in a proximal direction towards the housing and opened by movement of the rod in the opposite distal direction from the housing towards the jaws.

In addition to the claimed at least three floating pivots and in addition to the at least one fixed pivot and the claimed elements joining the pivots, the linkage structure may comprise further floating and/or fixed pivots and further rigid elements.

The first pivot could be movable suspended on the housing. This suspension may include a linear track formed in the housing and configured to limit movement of the first pivot such that it follows a substantially straight or a slightly curved line.

As described above, the movement of the handle towards the grip may either move the actuator element and thereby the jaws, or it may move the first pivot. Since the handle connects the second and third pivot, it will be the first pivot which will move as a substitute for the movement of the jaws.

Herein, the term closure force will describe the force needed to close the jaws in normal use when nothing is hindering free movement of the jaws. Release force will describe the force needed to move the first pivot and thereby release the pressure on the jaws. If the first pivot can move unhindered, or if the release force is less than the closure force, the first pivot will move as a substitute for jaw movement already before the jaws have started moving. For preventing this from happening, the movement of the first pivot may be limited by a constraint structure which ensures movement of the unhindered jaws before movement of the first pivot, i.e. which increases the release force so that it is higher than the closure force.

The constraint structure may comprise a spring-element which is deformable between a deformed and a relaxed state. The spring-element may e.g. be an elastically deformable element e.g. of plastic, rubber or of an elastically compressible foam material, or it may be a traditional spring, e.g. a helical spring, a disc spring, or it may be constituted by other spring structures known in the art. The constraint structure may e.g. be fixed to the housing, and it may particularly be housed in the grip portion of the housing.

The movement of the first pivot and/or the movement of the constraint structure relative to the housing could be facilitated by a lubricant. Particularly, the instrument may include at least a first lubricant between the first pivot and/or the constraint structure and the housing. The first lubricant could e.g. be silicone oil or similar non-toxic grease of oil. The first lubricant reduces the friction and therefore enables an earlier beginning of the movement, i.e. at relatively lower forces.

Other movable parts of the instrument may be lubricated with a second lubricant. For example, the aforementioned movable rod arranged in the shaft could be lubricated, and the movable knife could be lubricated. The second lubricant may preferably have a higher viscosity than the first lubricant.

In one example, the first lubricant is a medical grade white oil, e.g. having a kinematic viscosity in the range of 60-80 such as 70 or 71 mm/s at 40 degrees Celsius. The second lubricant may be a silicone oil, e.g. with a higher kinematic viscosity, e.g. in the range of 70-100 such as 80 or 90 mm/s at 40 degrees Celsius.

The handle is movable relative to the grip between a first and a second limit. The limits may e.g. be caused by mechanical limits and therefore provide end positions of the movement of the handle relative to the grip. The first limit may constitute a released handle and the second limit may constitute a completely depressed handle, i.e. a handle having reached the maximum distance from the released position.

The two limits are on opposite sides of an intermediate position. The movable pivots may particularly be arranged such that an intermediate position exist in which the first pivot, the second pivot, and the third pivot are positioned at three different positions along a first straight line, particularly a line which is non-parallel to the longitudinal direction of the shaft. E.g. along a straight line extending between 25-75 degrees to the longitudinal direction, such as 30-60 degrees, e.g. 40-50 degrees to the longitudinal direction.

Since the first pivot is connected to the second pivot by a first element and since the handle connects the second pivot and the third pivot, the mentioned intermediate position is one where the distance between the first and the third pivots are larger than for any other position of the handle relative to the housing. Movement of the handle away from the intermediate position thereby brings the first and third joints closer to each other irrespective whether it is towards the first or towards the second limit. During this movement, the second pivot moves away from the straight line between the first and the third pivots.

When the handle is in the first limit, the first, second, and third pivots are no longer along a straight line. In this configuration, a second straight line can be defined between the first and the third pivots and the second pivot is positioned at a distance, x, from that second straight line, where x is the shortest distance from the second pivot to the second straight line. The distance x may e.g. be in the range of 5-30 mm, such as in the range of 8-12 mm. such as in the range of 9-11 mm.

When the handle is in the second limit, a third straight line can be defined between the first and the third pivots and the second pivot is positioned at a distance, y, from that third straight line, where y is the shortest distance from the second pivot to the third straight line. The distance y may e.g. be in the range of 0.01-5 mm, such as in the range of 0.1-2 mm such as in the range of 0.5-1.5 mm.

Particularly, the ratio of x:y should be larger than 5 or even larger than 10 or even larger than 15.

The instrument according to the invention is preferably designed such that the jaws reach the closed position during movement of the handle from the first limit towards the intermediate position but before actually arriving at the intermediate position. When the jaws reach the closed position they can no longer move towards each other and for continued movement of the handle towards the intermediate position and towards the second limit, the first pivot will have to move as a substitute for the movement of the jaws. If movement of the first pivot is restricted by the constraint structure, the handle will have two relaxed positions, one on each side of the intermediate position—i.e. the force needed to move the handle will increase when moving the handle from the first limit towards the intermediate position and when moving the handle from the second limit towards the intermediate position. In this way, the handle may be movable in a first zone between the first limit and the intermediate position for moving the jaws, and the handle may be moved further whereby it passes the intermediate position. When the handle is moved in a second zone between the intermediate position and the second limit, the jaws becomes locked in the closed position. For releasing the lock, the handle must be moved in the second zone from the second limit towards and across the intermediate position against the force of the constraint structure.

The linkage structure thereby facilitates a simple and reliable locking mechanism which can hold the jaws locked by simply moving the handle across the intermediate position.

When the constraint structure is a spring-element, it may be arranged to become deformed when the first, the second, and the third pivots are positioned along the straight line, and the spring-element may particularly be arranged to be deformed in the direction of the straight line which can be defined by the first, second and third pivots in the intermediate position of the handle.

If the handle moves a much larger distance from the first limit to the intermediate position than from the intermediate position to the second limit, the user may obtain good ergonomic conditions. Particularly, it is easy to position the jaws precisely and the closure force may be acceptably low due to the large first zone whereas the process of locking and releasing the handle may become fast and easy by movement in the relatively short second zone. Accordingly, the ratio y:x may, as aforementioned, be in the range of at least 1:5.

The second element may connect the primary fixed pivot to the first pivot, or it may connect other fixed pivots to the first pivot. Particularly, the instrument may comprise at least 2 fixed pivots, herein referred to as primary fixed pivot and secondary fixed pivot.

If the second element connects the first pivot to the primary fixed pivot, then the spring-element may e.g. be arranged directly adjacent the first pivot to become deformed by contact with the first pivot. If the second element connects the first pivot to the secondary fixed pivot, then the spring-element may e.g. be arranged directly adjacent the second element such that it is deformed by direct contact with the second element.

The instrument may comprise a trigger which is movable between a released and an actuated position. The trigger allows operation by a finger and it is connected to a knife which is moved in a space between the jaws by movement of the trigger. In this embodiment, the linkage structure may prevent movement of the trigger when the jaws are in the open position. Particularly, the third pivot may move between a position where it is in the way for the trigger and a position where it allows movement of the trigger.

In a second aspect, the invention provides a method of obtaining a locked position of movable jaws in a handheld electrosurgical instrument which includes:

a housing forming a fixed grip;

a shaft extending in a longitudinal direction from a proximal end to a distal end, the proximal end being attached to the housing;

a jaw assembly attached to the distal end of the shaft, the jaw assembly comprising first and second jaw members movable relative to each other between an open position where tissue can be received between the jaw members and a closed position where the tissue can be fixed between the jaw members, the jaws being movable by movement of a rod in the shaft; and a handle movable relative to the fixed grip thereby effecting movement of the rod in the shaft;

the method comprising providing at least a first, a second and a third floating pivots, the floating pivots being provided such that they are movable relative to the housing;

providing at least one pivot being fixed to the housing;

connecting the first pivot and the second pivot with a first element connecting the first pivot and the fifth pivot with a second element connecting the second and third pivots with the handle; and arranging a rotatable actuator element such that it can move the rod in the shaft when it rotates.

The method may particularly include the step of locking the position of the handle when the jaws are in the closed position. This may particularly be obtained by moving the handle from a first limit past an intermediate position where the first, the second, and the third pivots are on a straight line. Particularly, the method may be carried out with an instrument of the kind described relative to the first aspect of the invention.

In a third aspect, the invention provides a method for moving a knife out of a space between jaws of an instrument of the kind descripted herein. The method comprises the steps of moving the handle distally towards a released position until mechanical contact between an edge of the handle and the trigger is established, continuing the movement of the handle in the distal direction while pressing the trigger distally by the contact with the handle until the trigger is in its released position.

In a fourth aspect, the invention provides a handheld electrosurgical instrument for cutting, cauterizing, or coagulating tissue or vessels, the instrument comprising:
- a housing forming a fixed grip;
- a handle movable relative to the fixed grip;
- a shaft extending in a longitudinal direction from a proximal end to a distal end, the proximal end being attached to the housing;
- a jaw assembly comprising first and second jaw members attached to the distal end of the shaft and being movable relative to each other between an open position where tissue can be received between the jaw members and a closed position where the tissue can be fixed between the jaw members, the jaw assembly further comprising a rod movably arranged in the shaft and configured for moving the jaws between the open and closed positions;
- a bar element connected to the handle and to a point in the housing;
- an actuator element configured to move the rod in the shaft The actuator element is configured to move the rod inside the shaft when the actuator element is rotated around the pivot,
the handle is rotationally connected to the actuator element in a pivot, and in a different point in the handle rotationally connected the bar element,
the bar element, extending between a first pivot and a rotational connection between the first element and the handle, and where the first pivot is movably suspended on the housing
to enable traveling of the first pivot relative to the housing during activation of the handle, such that the distance of the travel depends on the closure of the jaws.

The first pivot could be suspended from the housing by an element that in the one end is connected to the first pivot and the second end is connected to the housing by an additional pivot.

The first pivot could be movably suspended in the housing in a generally linear track formed in the housing.

The movement of the handle towards the grip may either move the actuator element and thereby the jaws, or it may move the first pivots. Since the handle connects the first bar element and actuator element, it will be the first pivot which will move as a substitute for the movement of the jaws.

The handle is movable relative to the grip between a first and a second limit. The limits may e.g. be caused by mechanical limits and therefore provide end positions of the movement of the handle relative to the grip. The first limit may constitute a released handle and the second limit may constitute a completely depressed handle.

The two limits are on opposite sides of an intermediate position. The movable pivots may particularly be arranged such that an intermediate position exist in which the first pivot, the connection between the bar element and handle, and the connection between the actuator element and the handle are positioned at three different positions along a first straight line, particularly a line which is non-parallel to the longitudinal direction of the shaft. E.g. along a straight line extending between 25-75 degrees to the longitudinal direction, such as 30-60 degrees, e.g. 40-50 degrees to the longitudinal direction.

The linkage system constituted by the bar element, the handle, the actuator and the housing comprises a number of pivots where the links are rotatable connected. The first pivot is moveable movably suspended in the housing, the second pivot connecting the bar element and the handle, a third pivot connecting the handle and the actuator element and a fourth pivot connecting the actuator element to the housing.

Since the first pivot is connected to the second pivot by a first bar element and since the handle connects the second pivot and the third pivot, the mentioned intermediate position is one where the distance between the first and the third pivots are larger than for any other position of the handle relative to the housing. Movement of the handle away from the intermediate position thereby brings the first and third pivots closer to each other irrespective whether it is towards the first or towards the second limit. During this movement, the second pivot moves away from the straight line between the first and the third pivots.

In the embodiment where the first pivot is suspended from the housing in a substantially linear track, and where the first pivot is therefore limited to move in a single direction along the track, the movement may particularly be along an axis substantially parallel with the line formed by the first, second and third pivots when the handle is in a locked position.

In one embodiment the first pivot is suspended from the housing via an element that connects the first pivot to an additional pivot fixed to the housing, then the spring-element may e.g. be arranged directly adjacent the first pivot to become deformed by contact with the first pivot. If the second element connects the first pivot to a pivot fixed to the housing, then the spring-element may e.g. be arranged directly adjacent the second element such that it is deformed by direct contact with the second element.

The instrument according to the fourth aspect of the invention may further be combined with the features mentioned for the instrument according to the first aspect of the invention. The invention further provides a method of operating the instrument according to the fourth aspect of the invention.

DETAILED DESCRIPTION OF THE INVENTION

In the following, embodiments of the invention will be described in further details with reference to the drawings in which.

It should be understood that the detailed description and specific examples, while indicating embodiments of the invention, are given by way of illustration only, since various changes and modifications within the spirit and scope of the invention will become apparent to those skilled in the art from the detailed description.

Figure 1:
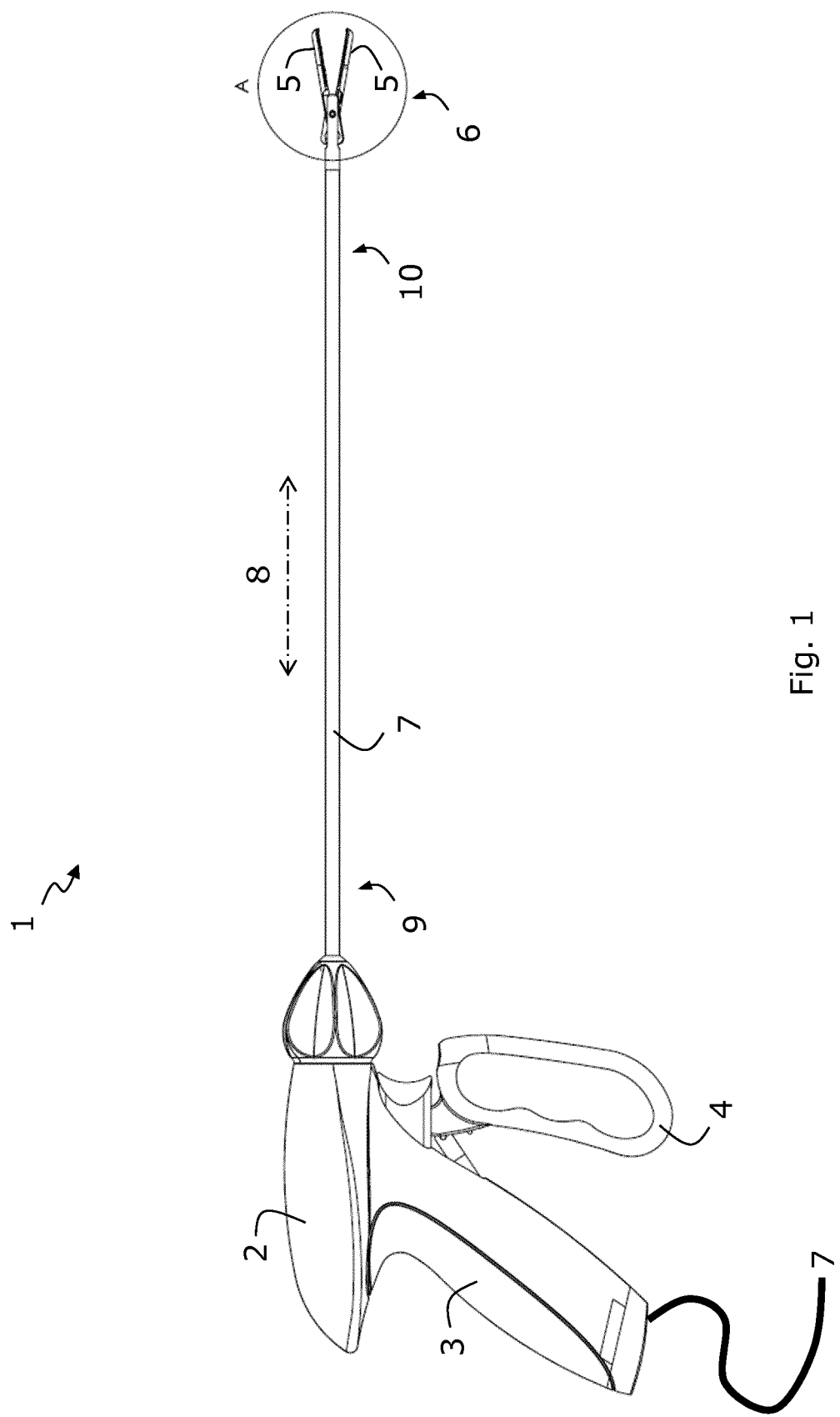
FIG. 1 illustrates a handheld electrosurgical instrument according to the invention.

FIG. 1 illustrates a handheld electrosurgical instrument 1 for cutting, cauterizing, or coagulating tissue. The instrument comprises a housing 2 forming an outer surface of the instrument and forming a fixed grip 3. A handle 4 is movable relative to the fixed grip and allows the surgeon to move the jaws 5 of the jaw assembly 6 between open and closed positions. The jaws are positioned at the distal end of the shaft 7. The shaft extends in a longitudinal direction, indicated by the arrow 8, from a proximal end 9, to the distal end 10 at which the jaw assembly 6 is attached. At the proximal end of the shaft, the shaft is attached to the housing.

FIGS. 2-8 illustrate the instrument in views where the housing and shaft are opened to visualize components inside the instrument. In this view, it can be seen that the jaw assembly further comprises a rod 11. The rod extends from the jaws through the shaft and into the housing. The rod can move in the longitudinal direction inside the shaft. In the distal end, the shaft is attached to the jaws in a joint which facilitate closing of the jaws when the rod moves proximally away from the jaws, and opening of the jaws when the rod moves distally in the direction towards the jaws.

The linkage structure is enclosed in the housing and arranged to transfer force from the handle to the rod such that the rod moves axially in the shaft when the handle is moved relative to the grip.

The linkage structure comprises the first pivot 12, which is connected to the second pivot 13 by a first rigid rod shaped element 14. The first pivot is connected to a fixed pivot 15 by a second rigid rod shaped element 16. The fixed pivot 15 is fixed rigidly to the housing 2.

The handle 4, or rather the bar shaped element 4' forming part of the handle 4, connects the second pivot 13 and the third pivot 17, and the third pivot 17 is connected to a primary one of the fixed pivots 18 by an actuator element 19. The actuator element 19 can rotate about the primary fixed pivot 18 whereby it moves the rod in the shaft.

Figure 2:
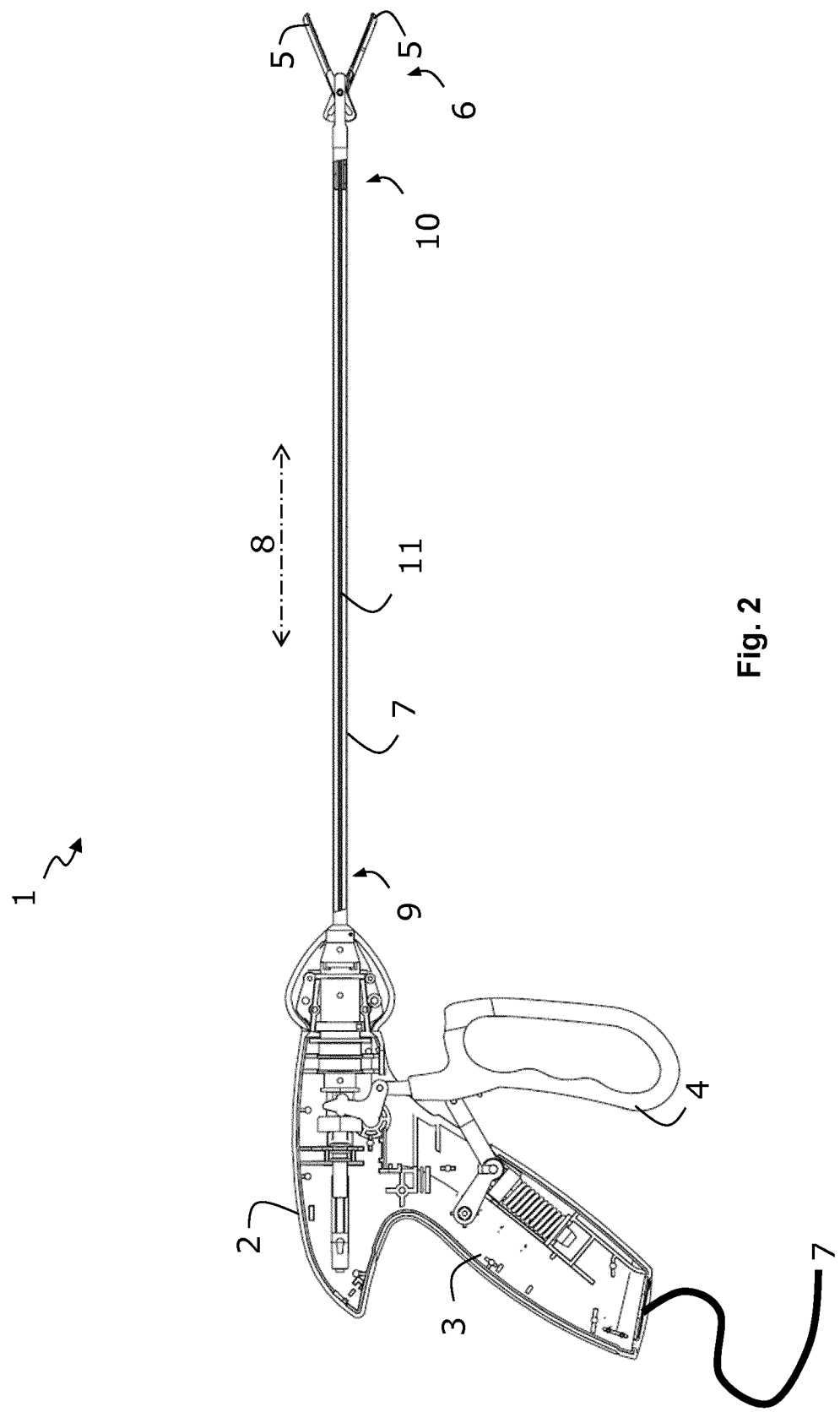
FIGS. 2-8 illustrate an open version of the instrument for visualization of internal parts.

FIG. 2 illustrates the instrument with the handle in a first limit position where the jaws are open.

Figure 3:
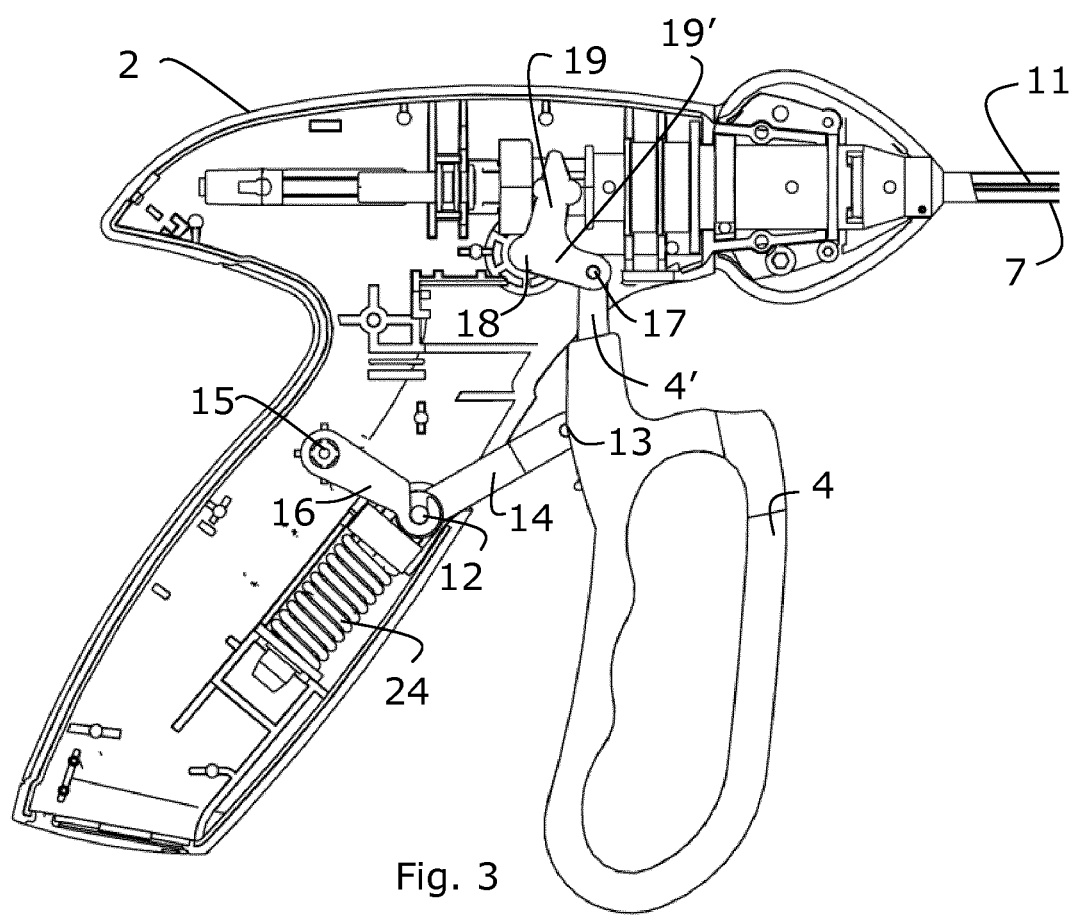

FIG. 3 illustrates an enlarged view of the housing and the linkage structure when the jaws are open, c.f. the configuration illustrated in FIG. 2. In this view, details of the linkage structure become clearer.

The pivots 15 and 18 are fixed to the housing and the housing thereby forms a rigid element between these two pivots. The linkage structure is thereby constituted by the bars 14, 16, 4', 19', and the bar which is formed by the housing, i.e. the bar existing between the pivots 15 and 18. The bars are linked by the pivots 12, 15, 13, 17, and 18. In the disclosed specific embodiment, the constraint structure is constituted by the spring 24. The spring 24 is compressible and allows movement of the pivot 12 in the handle. When the pivot 12 moves downwards away from the shaft, the movement is against the force from the spring, and when the pivot 12 moves upwards towards the shaft, the movement is supported by the force from the spring 24. The constraint structure, in the form of the spring 24, is shown in any of the FIGS. 2-3 and 5-8. The constraint structure provides resistance against movement of the first pivot. The constraint structure may also be constituted by other structural features whereby movement of the first pivot relative to the housing requires an increased force. As an example, movement of the first pivot may be limited by frictional resistance between the first pivot and the housing, by an elastically deformable coupling between the housing and the first pivot, or by other means. The movement may, correspondingly be limited by similar constraint structures working between one of the first and second elements and the housing, e.g. friction, springs, or other elastically deformable elements between the housing and one of the first and second elements.

Figure 4:
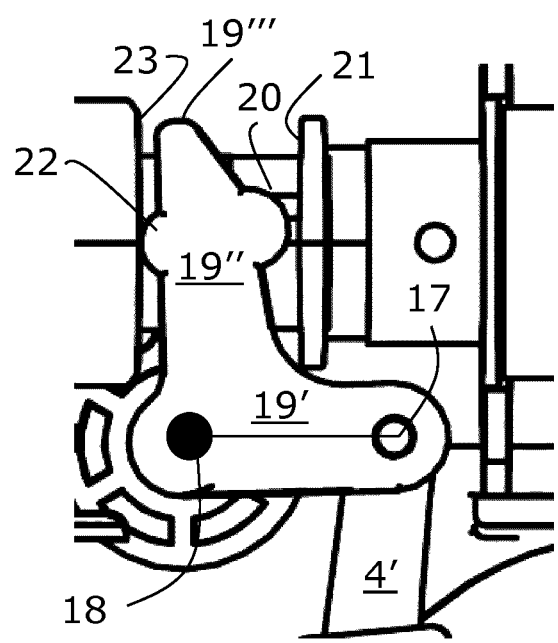

FIG. 4 illustrates further details of the actuator element 19 and its interaction with the rod 11 (the rod 11 is not illustrated in FIG. 4). The actuator element is triangular and forms a first leg between the pivots 17, 18. This leg forms one of the linkages in the 5-bar linkage structure. The actuator element 19 also forms a second leg 19" extending between the pivot 18 and the tip 19'''. This leg is used for manipulating the rod upon rotation of the actuator element 19 about the fixed pivot 18. Near the tip 19''', and more preferably, more than ⅔ of the distance between the pivot 18 and the tip 19''' away from the pivot 18, the second leg forms at least one and preferably 2 curved projections 20, 22. The projection 20 pushes against the flange 21 and thereby pushes the rod 11 distally towards the jaws, and the projection 22 pushes against the flange 23 and thereby pushes the rod 11 proximally away from the jaws. The projections 20, 22 are on opposite sides of the second leg, and essentially at equal distance from the line between the pivots 17, 18.

Figure 5:
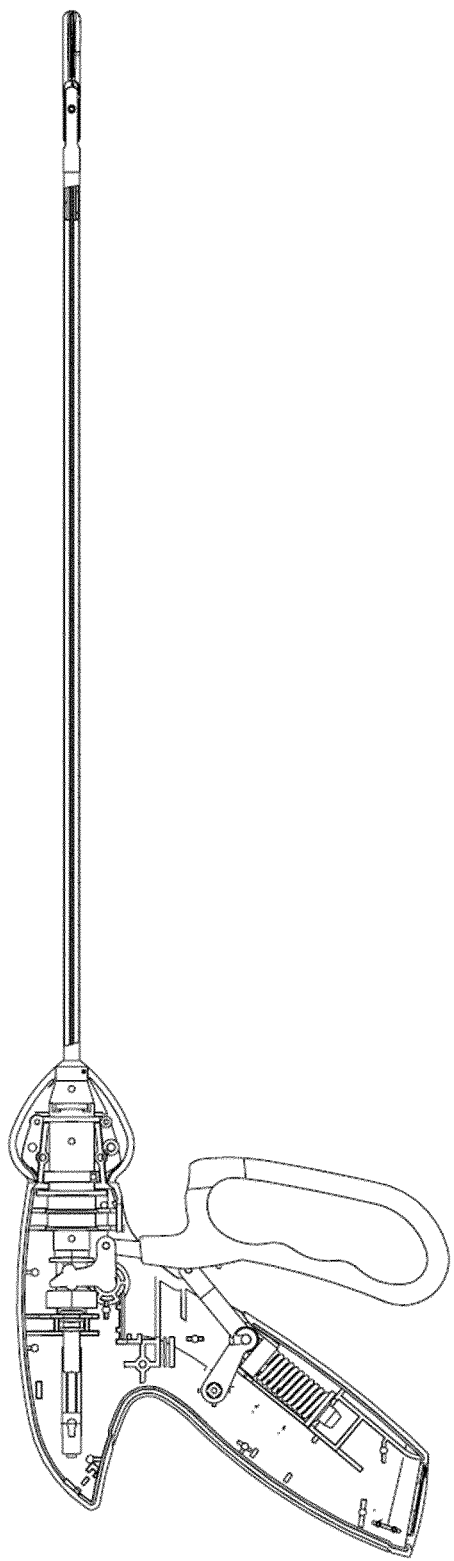
Figure 6:
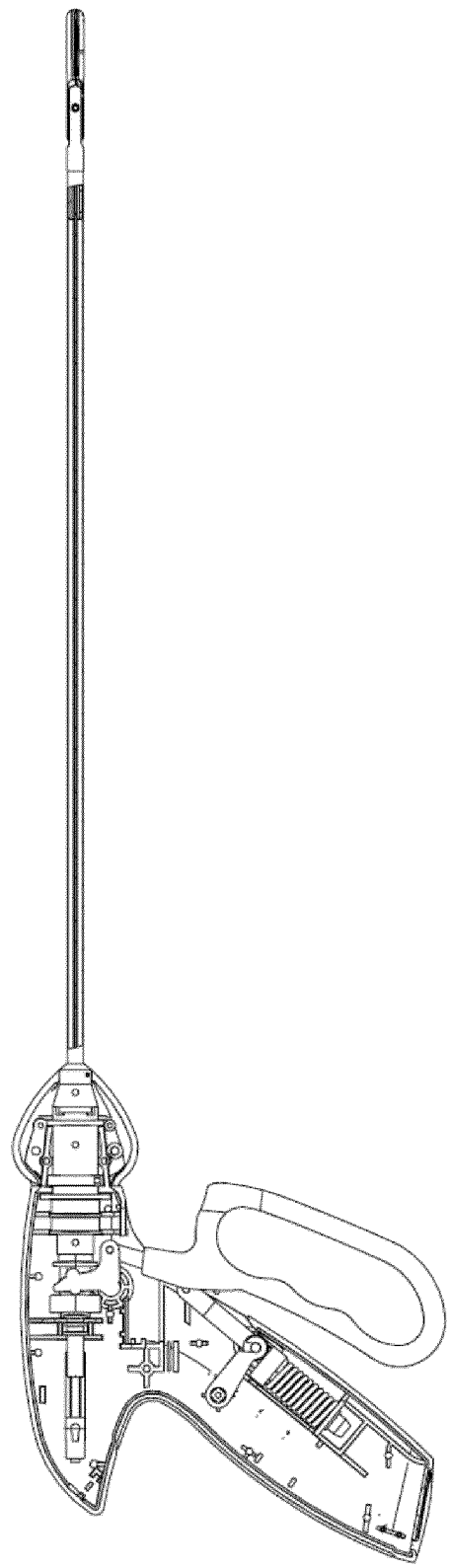

FIGS. 5 and 6 illustrate the instrument with the handle pressed towards the grip and therefore with the jaws closed.

The instrument forms an intermediate handle position in which the first, second and third pivots are on a straight line. In this position, the first pivot 12 has moved downwards in the handle away from the third pivot 17, and following that movement, the spring 24 is compressed. In FIG. 5, the handle is in a position before the intermediate position just before the spring becomes compressed, and further depressing of the handle will bring the first, second and third pivots on a straight line.

FIG. 6 illustrates the instrument with the handle completely depressed, i.e. the handle is in the second limit whereby further movement of the handle towards the grip is prevented by contact between the handle and the housing or by other mechanical stop-means. In this position, the first pivot 12 is returned at least partly towards the original, first, position corresponding to the released handle. Accordingly, the compression force stored in the spring is at least partly released, and movement of the handle back towards the first position will require renewed compression of the spring. Accordingly, a latched position of the handle is obtained by the combination between the floating first pivot 12 and the constraint structure, in this case constituted by the spring 24.

In use, the handle can be moved from the first limit shown in FIG. 2 towards the second limit shown in FIG. 3. During this movement two different results may be achieved:

1. During unhindered movement of the jaws, movement of the handle to the second limit will firstly rotate the actuator element about the primary fixed pivot and thereby move the jaws towards each other, c.f. difference between FIGS. 2, 3 and FIG. 5. When the jaws reach the closed position, continued movement of the handle, c.f. FIG. 6, will move the first pivot against the resistance of the constraint structure. During this movement, the surgeon will feel the resistance of the constraint structure against the movement of the handle, but the movement of the handle may continue. When reaching the intermediate position illustrated in FIG. 3, the spring or similar elastically deformable element is compressed, and further movement of the handle towards the second limit will return the second pivot and thus release at least a part of the compression of the spring. Accordingly, the handle can remain in this position without being held by the surgeon—i.e. a locked handle position is obtained.

2. During movement of the handle when the jaws are blocked, e.g. by thick layers of tissue, or blood vessels etc. the jaws move until the closure force which is required to close the jaws exceeds the force required to move the first pivot. At that point, the jaws stop moving, and the first pivot moves as a substitute for the movement of the jaws until the handle reaches the second limit. Accordingly, the surgeon can press the handle as hard as he wishes knowing that the linkage structure and constraint structure will ensure that the jaw force will not become excessive. In fact, the closure force will always be the same no matter how hard the handle is forced towards the grip.

FIGS. 2 and 3 illustrate the handle in the first limit, and FIG. 6 illustrates the handle in the second limit.

Figure 7:
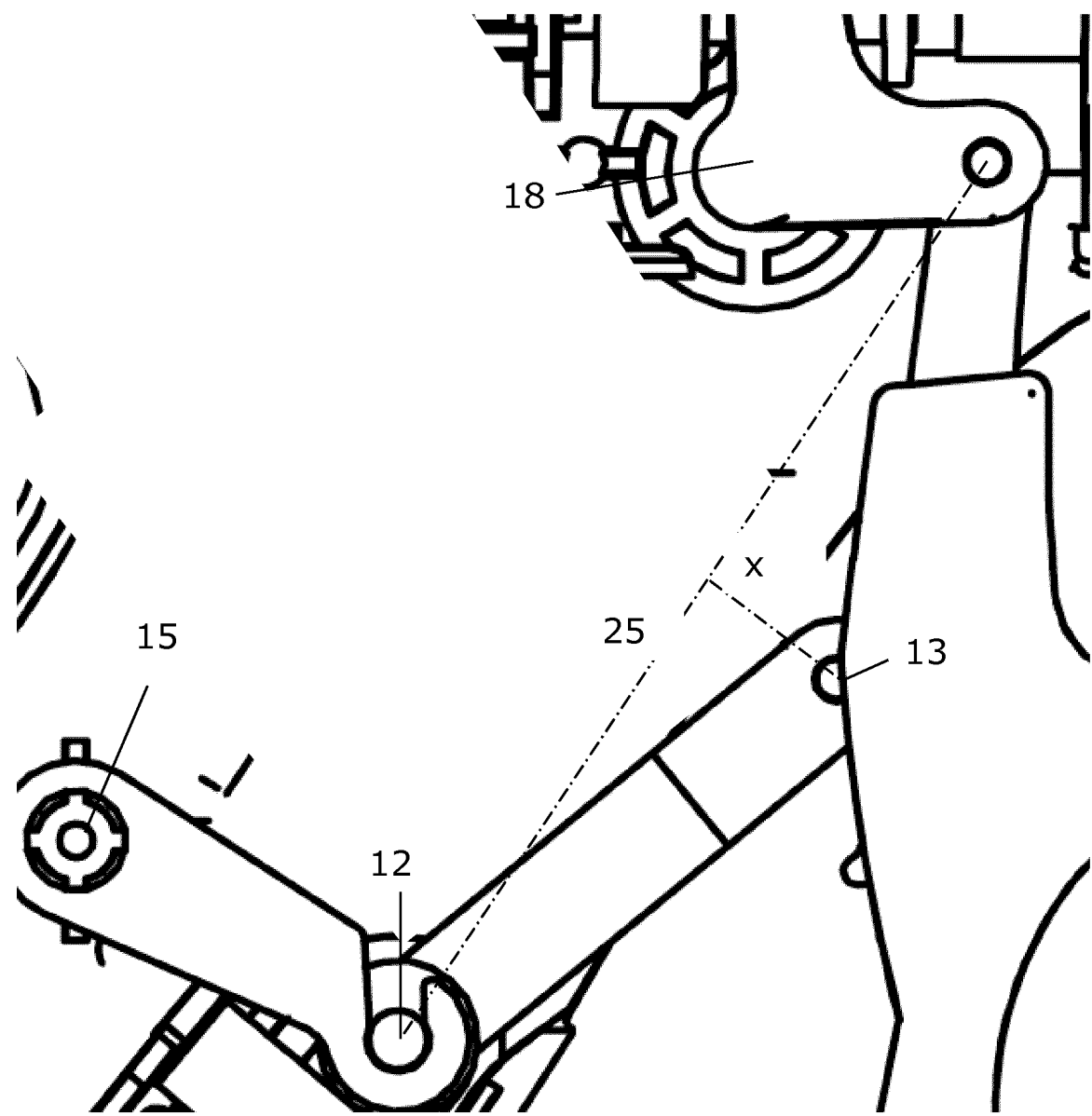

FIG. 7 illustrates enlarged details of the linkage structure when the handle is in the first limit. The first and third pivots are positioned along a second straight line, illustrated by the dotted line 25. In this position of the handle, the second pivot 13 is at a longest possible distance, illustrated by the dotted line, x, from the second straight line.

Figure 8:
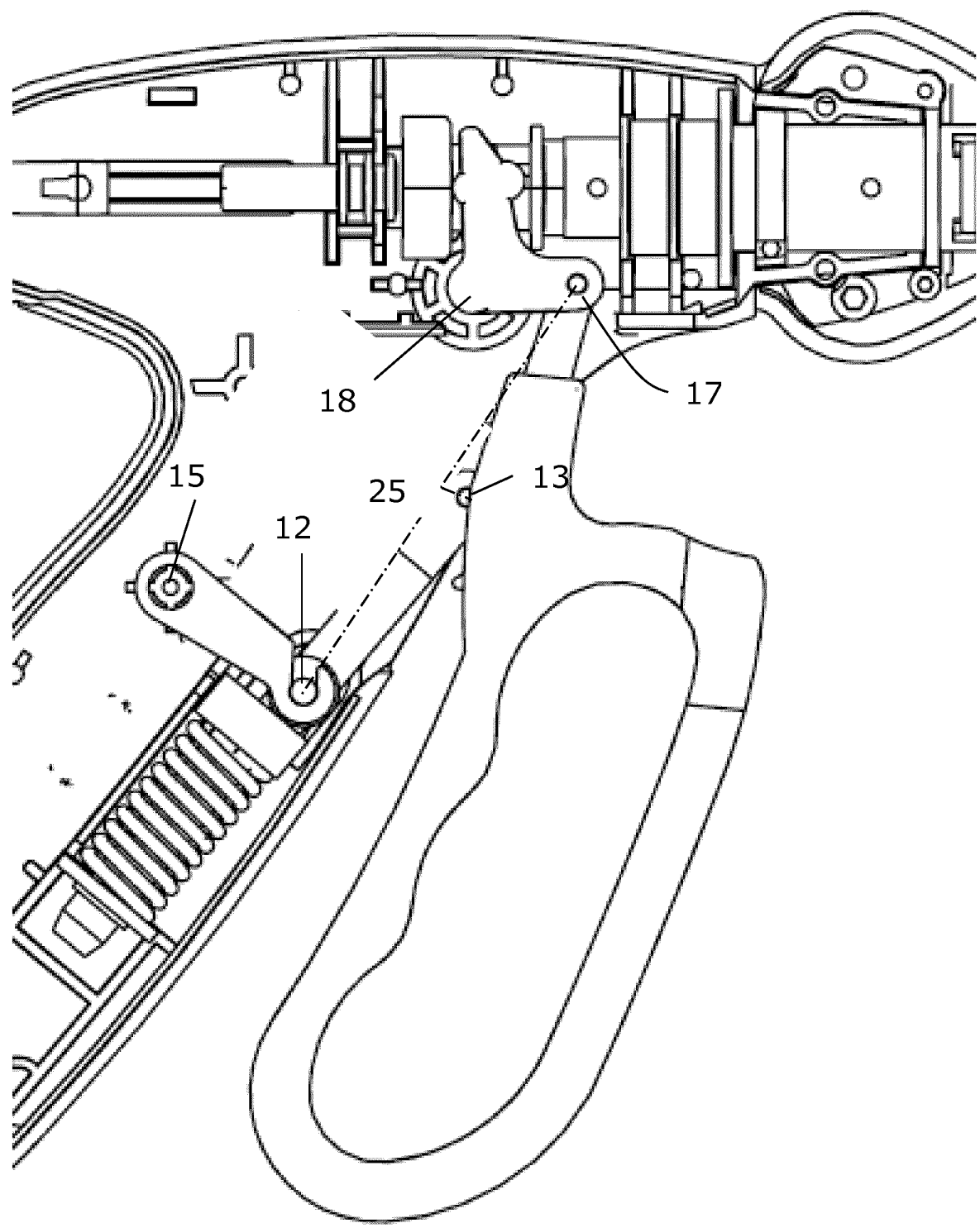

FIG. 8 illustrates an enlarged view of the linkage structure when the handle is pressed towards the second limit. In the illustrated position, the handle has not yet reached the intermediate position in which the first, second and third pivots are on a straight line, but the distance from the second pivot 13 to the dotted line 25 between the first and third pivots 12, 17 has been reduced. The distance x may be as much as 10 mm or more.

When the handle reaches the second limit, i.e. when it is completely depressed, the second pivot will be on the other side of the dotted line. In this document we refer to the distance on this opposite side between the second pivot 13 and the dotted line with the letter "y". This distance may e.g. be in the range of 0.01-5 mm, such as in the range of 0.1-2 mm such as in the range of 0.5-1.5 mm.

Particularly, the ratio of x:y should be larger than 5 or even larger than 10 or even larger than 15.

Figure 9:
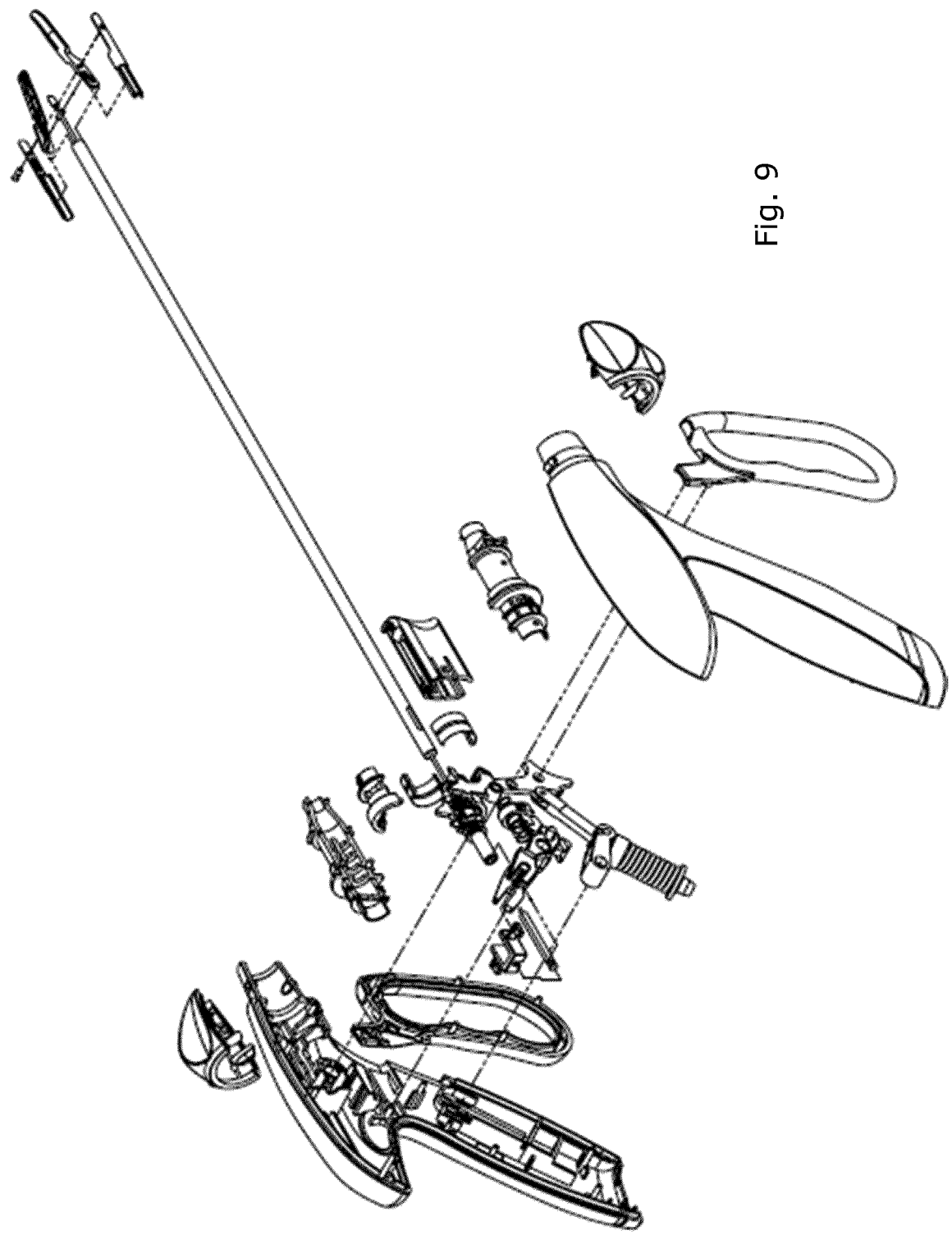
FIG. 9 illustrates an exploded view of the instrument.

FIG. 9 illustrates an exploded view including the linkage structure and the constraint structure.

The instrument may typically include a bipolar knife, a mono-polar knife, or a non-electrical, mechanically sharpened knife. The knife is used for cutting the tissue after coagulation.

Figure 10:
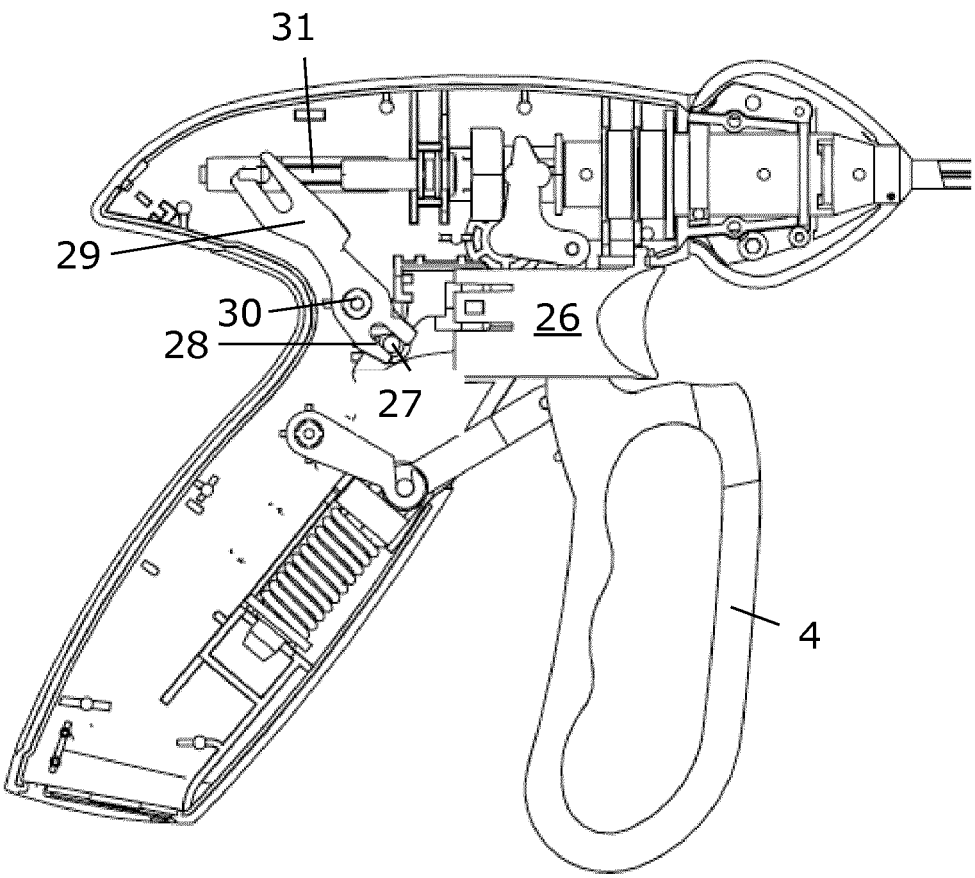
FIGS. 10-11 illustrate details of a trigger for a knife.

FIG. 10 illustrates the instrument including a trigger 26 located above the handle 4. The illustrated trigger is in a released position and can be moved in the proximal direction, i.e. away from the jaws, towards an actuated position. Correspondingly, the handle 4 is in the released position and can be moved in the proximal direction, i.e. away from the jaws, towards a completely depressed position.

The trigger, when moved from the released to the actuated position, translates a pinion 27 which engages a slot 28 in the knife arm 29 and thereby rotates the knife-arm about the knife-pivot 30. By rotation of the knife-arm, the knife-rod 31 is brought forward inside the shaft, and the knife is moved into the space between the jaws.

Figure 11:
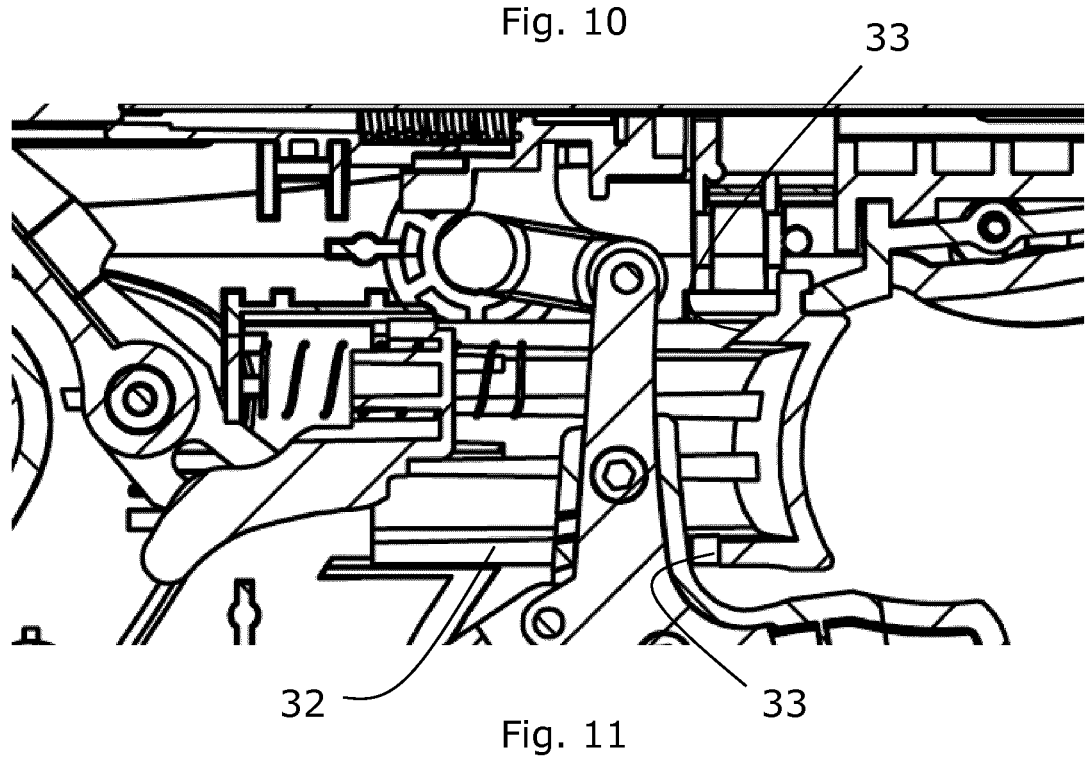

FIG. 11 illustrates an enlarged view of the trigger 26. The trigger is illustrated in a cross-section in which it can be seen that the trigger forms a slot 32 and that the trigger is arranged about the handle 4, or rather about the bar shaped element 4' of the handle. In the cross-section, the slot 32 has no cross-hatching whereas the trigger, where the slot ends, has cross-hatching to illustrate the cross-section.

The slot forms, in its closed end, an edge 33 which abuts the handle 4, or which at least would come in contact with the handle 4 if the trigger was moved to the actuated position while the handle is in the released position. The mechanical contact between the edge 33 and the handle 4 thereby prevent the trigger to be actuated and the knife to be moved distally into the space between the jaws unless the handle is depressed and the jaws therefore are in the closed position. This increases safety and prevents injury with unintended cutting with the knife.

Once the handle is moved to the depressed position, the trigger can be moved to the actuated position.

When the trigger is released, it is brought back to the released position and the knife is pulled out of the space between the jaws by use of a spring. If the knife sticks to the tissue, and therefore does not return out of the space between the jaws, the handle 4 can be moved to force the trigger to the released position by a solid handgrip. For this purpose, the handle may preferably be shaped with a first face 34 being used for depressing the handle, and with a second face 35 being useful for pulling the handle back to the released position, and thereby, if necessary for pulling the trigger to the released position.

Numbered Embodiments

1. A handheld electrosurgical instrument (1) for cutting, cauterizing, or coagulating tissue or vessels, the instrument comprising:
   a housing (2) forming a fixed grip (3);
   a handle (4) movable relative to the fixed grip;
   a shaft (7) extending in a longitudinal direction from a proximal end (9) to a distal end (10), the proximal end being attached to the housing;
   a jaw assembly (6) comprising first and second jaw members (5) attached to the distal end of the shaft and being movable relative to each other between an open position where tissue can be received between the jaw members and a closed position where the tissue can be fixed between the jaw members, the jaw assembly further comprising a rod (11) movably arranged in the shaft and configured for moving the jaws between the open and closed positions;
   a bar element (14) connected to the handle and to a point in the housing;
   an actuator element (19) configured to move the rod in the shaft The actuator element is configured to move the rod inside the shaft when the actuator element is rotated around the pivot (18), the handle (4) is rotationally connected to the actuator element in a pivot (17), and in a different point in the handle rotationally connected to the bar element (14), the bar element (14), extending between a first pivot and a rotational connection (13) between the first element and the handle, and where the first pivot (12) is movably suspended on the housing to enable traveling of the first pivot (12) relative to the housing during activation of the handle, such that the distance of the travel depends on the closure of the jaws.

2. An instrument according to embodiment 1, where the first pivot is suspended from the housing by an element (16) that in the one end is connected to the first pivot and in the second end is connected to the housing by an additional pivot (15).

3. An instrument according to embodiment 1 or 2, where the first pivot is movably suspended in the housing in a generally linear track formed in the housing.

The invention claimed is:

1. A handheld electrosurgical instrument for cutting, cauterizing, or coagulating tissue, the instrument comprising:
   a housing forming a fixed grip;
   a handle movable relative to the fixed grip;

a shaft extending in a longitudinal direction from a proximal end to a distal end, the proximal end being attached to the housing;

a jaw assembly comprising first and second jaw members attached to the distal end of the shaft, at least one of the first and second jaw members being movable relative to the other of the first and second jaw members between an open position where tissue can be received between the jaw members and a closed position where the tissue can be fixed between the jaw members, the jaw assembly further comprising a rod movably arranged in the shaft and configured for moving the jaw members between the open and closed positions; and a linkage structure for transferring force from the handle to the rod;

wherein the linkage structure comprises at least a first, a second, and a third floating pivots each being movable relative to the housing, and at least one fixed pivot being attached to the housing;

wherein the first pivot is connected to the second pivot by a first element;

wherein the first pivot is connected to one of the at least one fixed pivots by a second element;

wherein the handle connects the second pivot and the third pivot;

wherein the third pivot is connected to a primary one of the fixed pivots by an actuator element which is arranged to move the rod in the shaft upon rotation about the primary fixed pivot;

wherein the handle is movable relative to the grip between a first limit and a second limit, the first limit and second limit being on opposite sides of an intermediate position, and wherein the first pivot, the second pivot and the third pivot are positioned along a first straight line when the handle in in the intermediate position.

2. The instrument according to claim 1, further comprising a constraint structure limiting movement of the first pivot such that the jaw members, during movement of the handle while the jaw members are free to move relative to each other, moves to the closed position before the first pivot moves.

3. The instrument according to claim 2, where the constraint structure is configured to increase a release force which is necessary for moving the first pivot relative to the housing such that the release force becomes higher than a closure force which is needed for moving the jaw members to the closed position under normal use when nothing is hindering free movement of the jaw members relative to each other.

4. The instrument according to claim 2, where the constraint structure comprises a spring-element reversibly deformable between a deformed and a relaxed state.

5. The instrument according to claim 4, where the first and third pivots are positioned along a second straight line when the handle is in the first limit, and the second pivot is at a distance x from the second straight line, where x is in the range of 10-30 mm.

6. The instrument according to claim 5, where the first and third pivots are positioned along a third straight line when the handle is in the second limit, and the second pivot is at a distance y from the third straight line, where y is in the range of 1-10 mm.

7. The instrument according to claim 6, where a ratio x:y is at least 5 and not greater than 30.

8. The instrument according to claim 6, where at least one of the first, the second and the third straight lines is transverse to the longitudinal direction.

9. The instrument according to claim 8, where the first straight line extends at an angle between 25 and 75 degrees to the longitudinal direction.

10. The instrument according to claim 6, where the spring-element becomes deformed along one of the first, the second and the third straight lines.

11. The instrument according to claim 4, where the spring-element is arranged to become deformed when the first, the second, and the third pivots are positioned along the first straight line.

12. The instrument according to claim 4, where the first pivot is connected to the primary fixed pivot by the second element.

13. The instrument according to claim 12, where the spring-element is arranged directly adjacent the first pivot to become deformed by contact with the first pivot.

14. The instrument according to claim 4, where the spring-element is arranged to become deformed at least upon movement of the first pivot relative to the housing.

15. The instrument according to claim 1, where the first pivot is movably suspended in the housing in a generally linear track formed in the housing.

16. The instrument according to claim 1, further comprising a secondary fixed pivot, the first pivot being connected to the secondary fixed pivot by the second element.

17. The instrument according to claim 16, further comprising spring-element arranged directly adjacent the second element to become deformed by contact with the second element.

18. The instrument according to claim 1, comprising a trigger movable between a released and an actuated position, and a knife movable in a space between the first and second jaw members upon movement of the trigger, wherein the linkage structure prevents movement of the trigger from the released to the actuated position when the jaw members are in the open position.

19. The instrument according to claim 18, where the third pivot prevents movement of the trigger from the released to the actuated position.

20. The instrument according to claim 1, where the actuator element forms a first and a second leg, the first leg extending between the third pivot and the primary one of the fixed pivots, and the second leg comprises at least two oppositely directed projections arranged to cooperate with flanges of the rod to thereby move the rod in the shaft.

21. A method of obtaining a locked position of at least one movable jaw member in a handheld electrosurgical instrument which includes:

a housing forming a fixed grip;

a shaft extending in a longitudinal direction from a proximal end to a distal end, the proximal end being attached to the housing;

a jaw assembly attached to the distal end of the shaft, the jaw assembly comprising first and second jaw members movable relative to each other between an open position where tissue can be received between the jaw members and a closed position where the tissue can be fixed between the jaw members, the jaw members being movable by movement of a rod in the shaft; and a handle movable relative to the fixed grip thereby effecting movement of the rod in the shaft;

the method comprising:

providing at least a first, a second and a third floating pivots, the floating pivots being provided such that they are movable relative to the housing;

providing at least one pivot being fixed to the housing;

connecting the first pivot and the second pivot with a first element;
connecting the first pivot and a fifth pivot with a second element;
connecting the second and third pivots with the handle; and
arranging a rotatable actuator element such that it can move the rod in the shaft when it rotates;
wherein the handle is movable relative to the grip between a first limit and a second limit, the first limit and second limit being on opposite sides of an intermediate position, and
wherein the first pivot, the second pivot and the third pivot are positioned along a first straight line when the handle is in the intermediate position.

* * * * *